United States Patent [19]
Tessmann et al.

[11] Patent Number: 6,132,402
[45] Date of Patent: Oct. 17, 2000

[54] STORAGE AND DELIVERY DEVICE FOR A CATHETER OR NEEDLE

[75] Inventors: Terri L. Tessmann, Racine; Charles J. Patrick, Milwaukee, both of Wis.

[73] Assignee: Bioform Inc., Franksville, Wis.

[21] Appl. No.: 09/240,703

[22] Filed: Feb. 2, 1999

[51] Int. Cl.[7] .................................................. A61M 5/00
[52] U.S. Cl. .......................... 604/240; 604/243; 285/305
[58] Field of Search ................................... 604/181, 240, 604/242, 243, 232, 234, 533, 187, 905; 285/305, 385

[56] References Cited

U.S. PATENT DOCUMENTS

| | | | |
|---|---|---|---|
| 2,147,616 | 2/1939 | Chaput . | |
| 2,737,950 | 3/1956 | Berthiot . | |
| 2,830,586 | 4/1958 | Dann et al. . | |
| 2,830,596 | 4/1958 | Dann et al. . | |
| 3,424,158 | 1/1969 | Silver . | |
| 4,084,588 | 4/1978 | Koenig . | |
| 4,436,125 | 3/1984 | Blenkush | 604/905 |
| 4,445,896 | 5/1984 | Gianturco | 604/238 |
| 4,900,307 | 2/1990 | Kulli | 604/110 |
| 4,993,426 | 2/1991 | Spencer | 128/763 |
| 5,013,300 | 5/1991 | Williams | 604/119 |
| 5,117,837 | 6/1992 | Wannamaker et al. | 128/763 |
| 5,158,569 | 10/1992 | Strickland et al. . | |
| 5,456,673 | 10/1995 | Ziegler et al. | 604/264 |
| 5,586,977 | 12/1996 | Dorsey, III | 604/264 |
| 5,603,696 | 2/1997 | Williams et al. | 604/93 |
| 5,797,490 | 8/1998 | Fujii et al. | 206/365 |

OTHER PUBLICATIONS

Medical Equipment Designer, Jan. 1999, p. M19, "Quick Disconnect Couplings".
Cole–Palmer Instrument Company, Sales Brochure, p. 311.
ProConnect Sales Brochure, pp. 4, 5 and 8.
VWR Scientific Product Brochure, pp. 1768 and 1770.

*Primary Examiner*—Wynn Wood Coggins
*Assistant Examiner*—Kevin C. Sirmons
*Attorney, Agent, or Firm*—Foley & Lardner

[57] ABSTRACT

A storage and delivery device for a highly viscous material comprising a delivery cap for connecting a catheter or needle to a cartridge, an interconnect insert and a compression sleeve disposed within the delivery cap for creating a leak proof seal between the cartridge and the delivery cap, and a slide lock to reliably lock the cartridge to the delivery cap. The slide lock includes two holes of a first and second diameter arranged in a figure-eight shape for positively securing the delivery cap to a cartridge.

40 Claims, 10 Drawing Sheets

STORAGE AND DELIVERY DEVICE FOR A CATHETER OR NEEDLE

BACKGROUND OF THE INVENTION

1. Field of the Invention

The present invention relates generally to a storage and delivery system for a highly viscous material. More specifically, the invention relates to a delivery system which supplies a highly viscous material from a syringe to a catheter or a needle for injection purposes.

2. Description of the Related Art

Figure 1:
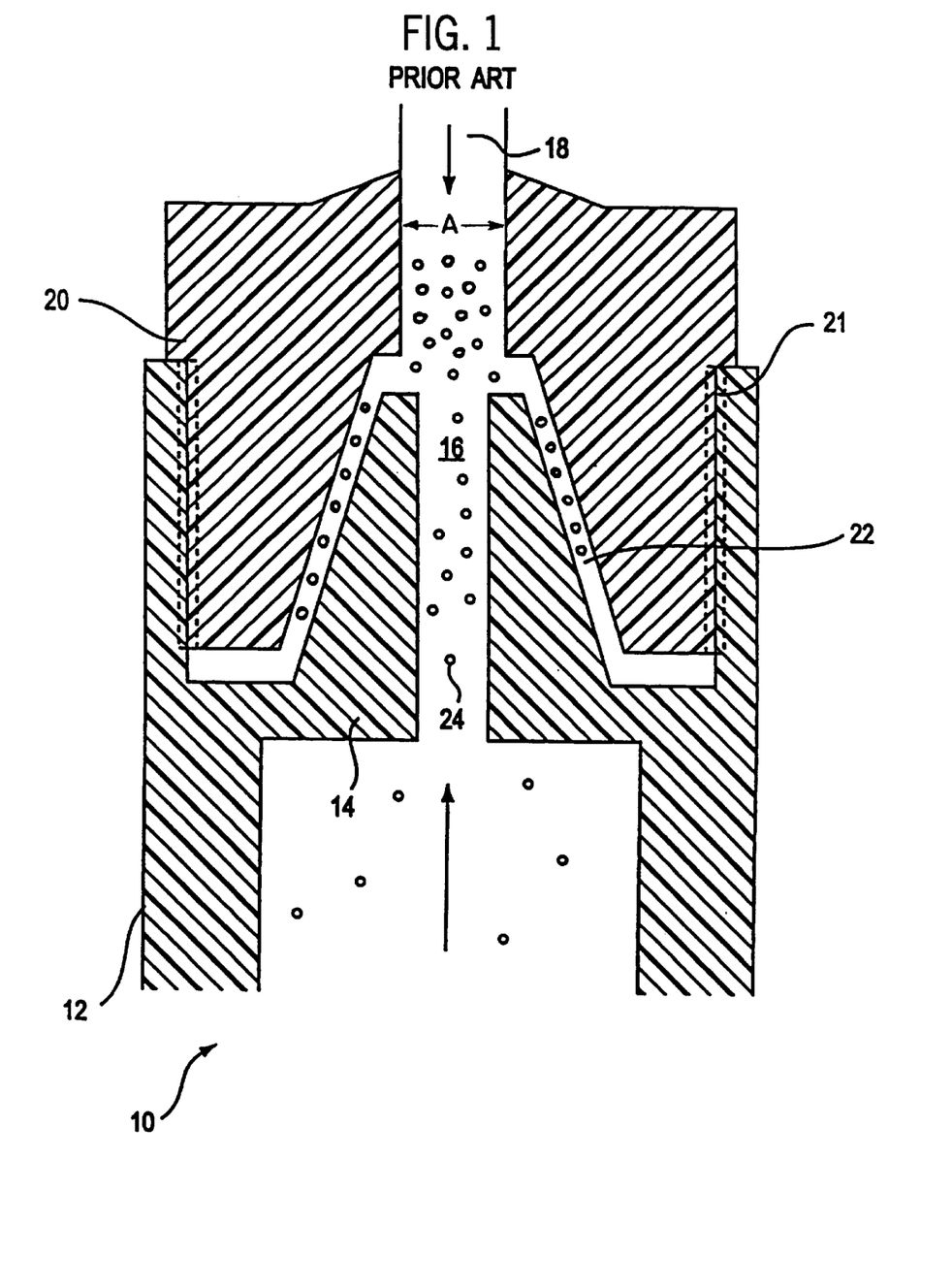
FIG. 1 is a cross-sectional view of a prior art device.

FIG. 1 shows a prior art device for supplying a fluid to a catheter or needle. The barrel 12 of the syringe 10 has a conical hub 14 formed at an end thereof for dispensing a material 16 stored in the syringe to a catheter or needle 18. The hub 14 is connected to the catheter or needle 18 through a cap 20 which is threadedly attached to the inside portion of an extended portion 21 of the barrel 12. The cap 20 is also cone-shaped and a seal is formed between the two mating conical surfaces of the hub and cap. The seal is tightened by further rotation of the cap 20. This type of device is sometimes referred to as a Luer lock fitting.

The problem with this device is as follows. Prior to the step of attaching the cap 20 to the hub 14, the material 16 may inadvertently contaminate the outer conical shape of the hub 14. In certain applications, the material 16 includes a viscous gel with coarse particles 24 suspended therein such as CoapTite™. The presence of the particles 24 on the conical surface of the hub prevents a tight seal from being formed by the mating conical surfaces of the cap 20 and hub 14. As a result, when the plunger (not shown) of the syringe 10 is actuated to force the material 16 into the catheter or needle 18, some of the gel leaks out through a narrow gap 22 between the conical surfaces of the hub 14 and the cap 20. When this occurs, the relative concentration of coarse particles in the viscous material that travels into the catheter or needle increases, which increases the viscosity substantially. When certain materials are used, the viscosity increases to a level at which the material may not be able to travel through the catheter or needle. That is, even if the force exerted on the plunger of the syringe is increased dramatically, the material cannot be forced into the catheter or needle. Also, this excessive force may damage or break the syringe. If this happens, the catheter/needle delivery system must be replaced, which is expensive, inconvenient and potentially dangerous if the catheter/needle is being used for emergency treatment.

Also, in this prior art device, the end of the syringe where the material is dispensed to the catheter or needle has a reduced diameter A. When the viscous material travels through this reduced diameter portion, the pressure is increased, which further restricts the flow of the material to the catheter or needle.

Further, because the cap 20 is threadedly attached to the hub 14, in order to remove the syringe, it is necessary to rotate the cap 20, which is time consuming and cumbersome.

As an alternative to using screw threads, it is known in the art to utilize a locking slide to secure members in syringe devices. For example, U.S. Pat. No. 2,737,950 (Berthiot) discloses a cooperating lock 18 for securing a needle 10. As shown in FIG. 3 of Berthiot, the lock 18 has a large diameter portion and a narrow diameter portion formed by two web-shaped branches 19. When the needle 10 is moved down towards its operational position, the lower end 14 of the needle passes through the large diameter portion of the lock 18. When the needle reaches its operational position, the lock 18 is pushed so that the groove 20 of the needle is locked firmly into position by the two web-shaped branches 19.

Also, U.S. Pat. No. 5,158,569 (Strickland), discloses a slide plate 84 for securing a catheter 9. As shown in FIG. 3 of Strickland, the slide plate 84 includes a circular opening 94 having a diameter which is greater than the diameter of the catheter 9 and a slot 96 having a width which is less than the diameter of the catheter 9. When the slide plate is in a first, or retracted, position, the catheter 9 passes freely through the circular opening 94 (see FIGS. 4 and 5 of Strickland). When the slide plate is in a second, or inserted, position, the slot 96 frictionally engages the catheter, thereby restraining the catheter 9 in the slide plate 84 (see FIGS. 2 and 6 of Strickland).

When the slide locks disclosed by Berthiot and Strickland are moved to the locked position, these slide locks do not provide any positive indication to the user that the slide locks are properly engaged in the locked position. Therefore, there exists the possibility that the needle 10 and catheter 9 may be improperly secured by the slide lock.

SUMMARY OF THE INVENTION

The present invention has been made in view of these problems associated with the prior art. Accordingly, one of the objects of the present invention is to provide a delivery system which can reliably deliver a highly viscous material, even if the material contains coarse particles, to a needle or catheter which exhibits minimal or no leakage of the highly viscous material.

A second object of the present invention is to provide a delivery system in which it is easy to change the syringe.

A third object of the present invention is to provide a delivery system which can positively inform the user that the syringe is properly attached and locked thereto.

To achieve these objects, the delivery system of the present invention comprises a delivery cap for connecting a catheter or needle to a cartridge, an interconnect insert and a compression sleeve disposed within the delivery cap which create a leak proof seal between the cartridge and the delivery cap, and a slide lock to reliably lock the cartridge to the delivery cap.

With this configuration, the delivery system of the present invention can reliably supply a highly viscous material to a catheter or a needle with minimal leakage between the syringe and the delivery cap. Also, the syringe can be replaced easily without rotating the syringe. Further, when a syringe is attached to the delivery cap, the slide-lock assembly positively informs the use that the syringe is properly attached and locked to the delivery cap.

DESCRIPTION OF THE PREFERRED EMBODIMENTS

The details of the present invention will be described below.

Figure 2A:
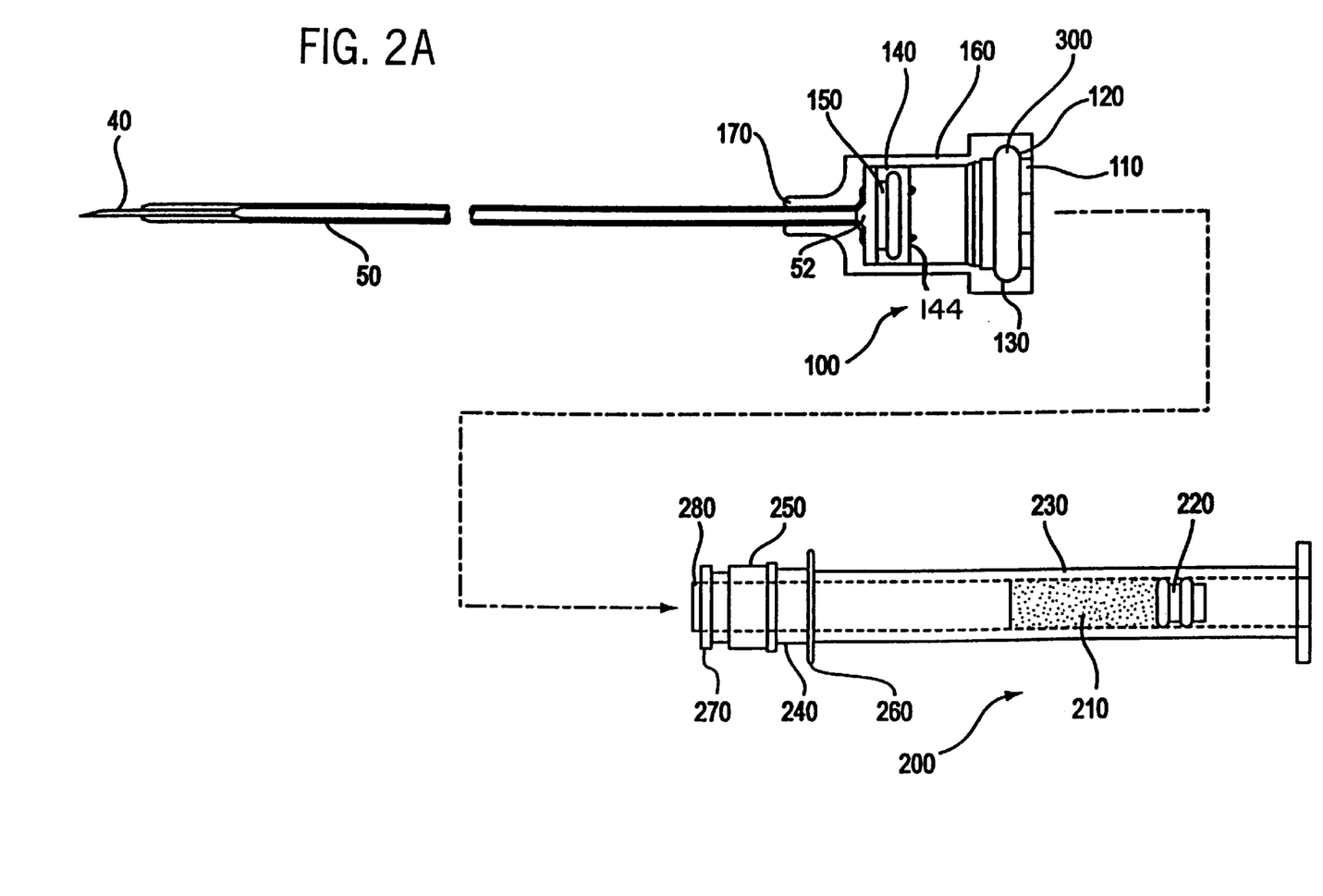
FIGS. 2A, 2B and 2C show the main components of a first embodiment of the present invention.
Figures 2B, 2C:
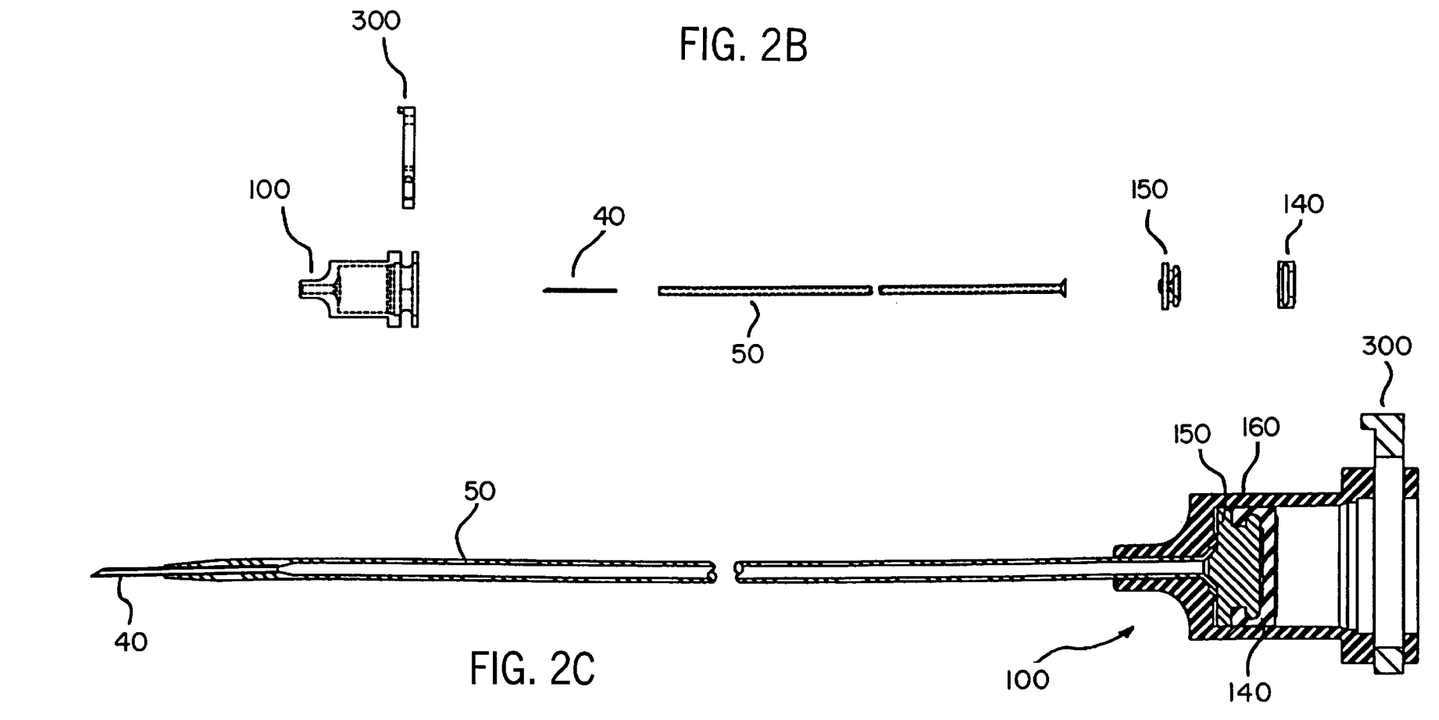

As shown in FIGS. 2A–2C, the main components of a first embodiment of the present invention include a delivery cap 100, a main housing or cartridge 200 which fits into an opening 110 of the delivery cap 100, and a locking clamp 300 provided in the delivery cap 100 for locking the cartridge 200 to the delivery cap 100. The cartridge stores a viscous material 210 which is supplied to the delivery cap 100 by the action of a plunger 220. A catheter 50 is attached to a distal end of the delivery cap 100 for supplying the viscous material 210 from the cartridge 200 to a needle 40 disposed at the end of the catheter 50.

Figure 9:
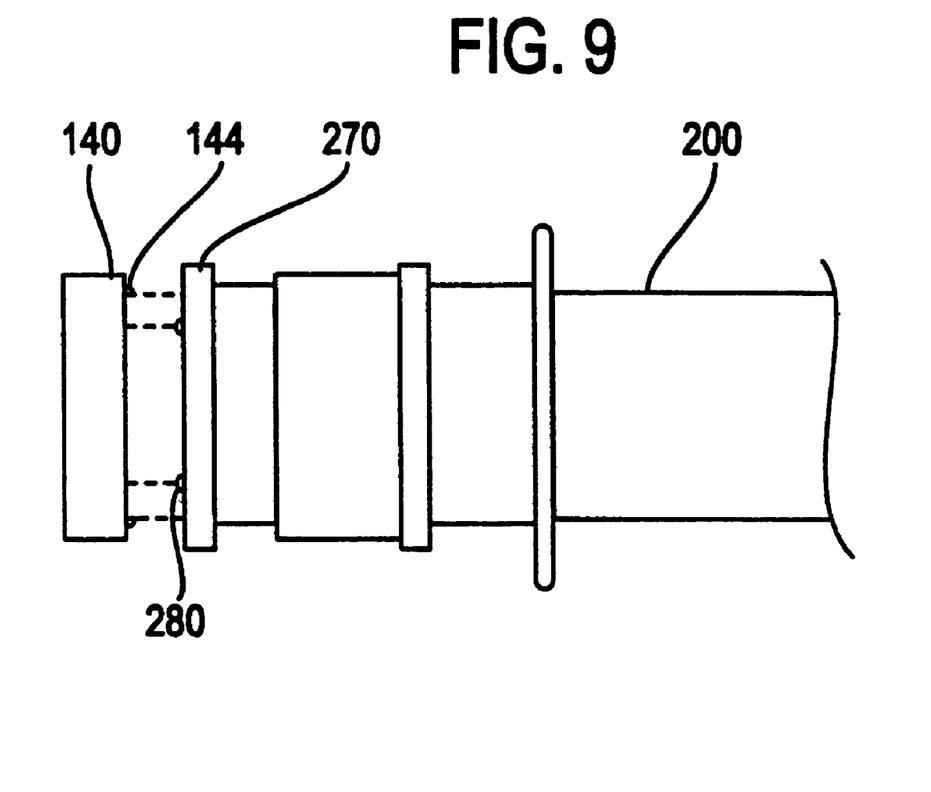
FIG. 9 shows the raised sealing surfaces of the cartridge mating with the raised sealing surfaces of the compression sleeve.

The delivery cap 100 includes a soft rubber compressive sleeve 140 disposed therein for creating a tight seal with a distal end 270 of the cartridge 200 which becomes pressed against the compressive sleeve 140 when the cartridge 200 is inserted into the delivery cap 100. As discussed above in the description of the prior art device, it is possible that the compressive sleeve 140 or distal end 270 will become contaminated with the particles of the gel material. Because the compressive sleeve 140 is made of soft rubber, these particles become embedded therein, thereby preventing the degradation of the seal between the cap 100 and cartridge 200 which occurred in the prior art device. Further, raised sealing ribs 144 and 280 are formed on the lower face of the compressive sleeve 140 and distal end 270 of the cartridge 200 (see FIGS. 2A, 7 and 9). These raised sealing ribs 144 and 280, which are offset from one another as shown in FIG. 9, further create a tight seal between the delivery cap and the cartridge.

Figure 6:
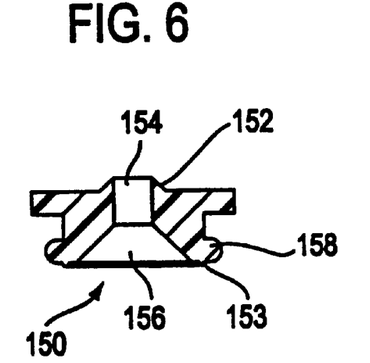
FIG. 6 is a cross-sectional view of the interconnect insert.
Figure 7:
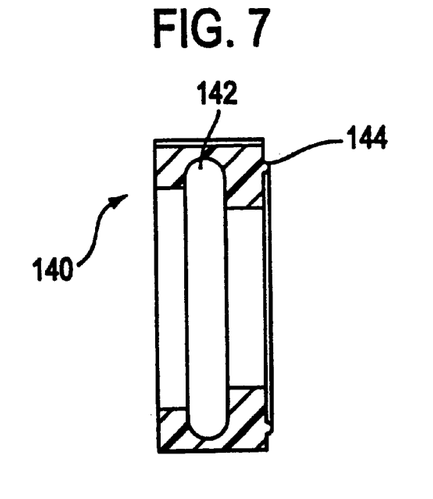
FIG. 7 is a cross-sectional view of the compression sleeve.

As shown in FIGS. 2A and 2C, a compression sleeve 140 is positioned adjacent to the interconnect insert 150 for forming a seal between a distal end 270 of the cartridge 200 and the delivery cap 100. As shown in FIG. 7, the compression sleeve 140 has a wide diameter cutout portion 142 for receiving a flange portion 158 of the interconnect insert 150, thereby to attach the interconnect insert 150 to the compression sleeve 140. The interconnect insert 150 and compression sleeve 140 do not necessarily have to be separate components and could be combined as one component. As shown in FIG. 6, a raised sealing rib 153 is formed on the lower surface of the interconnect insert 150. The raised sealing rib 153 improves the seal between the interconnect insert 150 and the compression sleeve 140.

Figure 8:
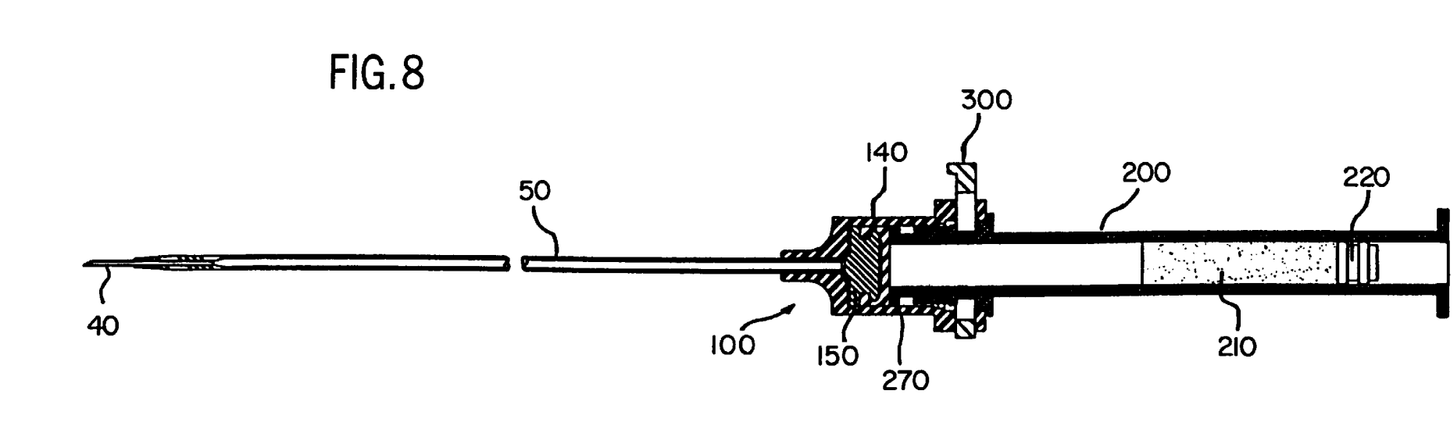
FIG. 8 is a cross-sectional view of the delivery cap attached to a cartridge.

As shown in FIG. 8, when the cartridge 200 is attached to the delivery cap 100 with the locking clamp 300, the distal end 270 of the cartridge 200 abuts against the compression sleeve 140. Accordingly, the diameter of the cartridge 200 at the dispensing site is the same as the inner diameter of the remaining portions of the cartridge 200. This large opening at the delivery end promotes the delivery of the viscous material to the catheter 50 and eliminates the need to increase the pressure substantially. In standard syringes which taper down into a slip-fit or luer lock fitting, it is necessary to increase the pressure substantially.

As shown in FIG. 7, a raised sealing rib 144 is formed on the lower face of the compression sleeve 140. Similarly, as shown in FIG. 2A, a raised sealing rib 280 is formed on the distal end 270 of the cartridge 200. As shown in FIG. 9, the diameter of the raised sealing rib 144 is greater than the diameter of the raised sealing rib 280 so that when the when the cartridge 200 presses against the compression sleeve 140, the raised sealing ribs 144 and 280 are offset. This offsetting of the raised sealing ribs 144 and 280 creates a tight seal between the cartridge 200 and the compression sleeve 140, thereby establishing a leak-proof connection between the cartridge 200 and the delivery cap 100.

Figure 5:
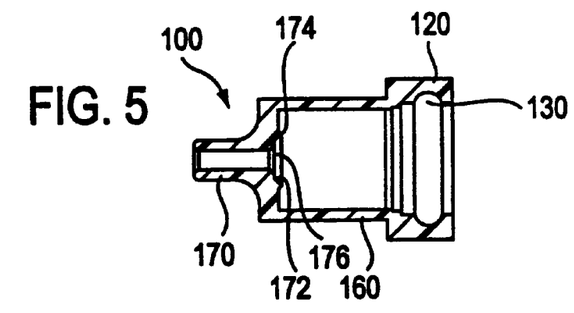
FIG. 5 is a cross-sectional view of the delivery cap.

As shown in FIG. 5, the delivery cap 100 includes a base 120, a central portion 160, and a nose portion 170. As presented above, a slot 130 is formed in the base 120 for accommodating the locking clamp 300. Sealing surfaces 172 and 174 are formed in conical cut-out section 176 of the nose portion 170.

As shown in FIGS. 2A–2C, an interconnect insert 150 is positioned inside the central portion 160 adjacent to the nose portion 170. As shown in FIG. 6, a raised central portion 152 is formed on the upper circular face of the interconnect insert 150. When the interconnect insert 150 is positioned in the delivery cap 100, the raised central portion 152 fits into the conical cutout section 176 (see FIGS. 2 and 5). The diameter of the conical cut-out section 176 is larger than the diameter of the raised central portion 152, thereby forming a conical-shaped gap between the nose portion 170 and the interconnect insert 150. As shown in FIGS. 2A and 2C, this conical-shaped gap accommodates a flared-out end portion 52 of the catheter 50. When the interconnect insert 150 is fixed to the inside edge of the nose portion 170 by ultrasonic welding or the like, the flared-out end portion 52 of the catheter 50 are pressed firmly between the raised central portion 152 and the sealing surfaces 172 and 174, thereby forming a leak-proof seal between the interconnect insert 150 and the catheter 50.

As shown in FIG. 6, the interconnect insert 150 has a centrally located cylindrical cut-out portion 154 and conical cut-out portion 156 which together form a passageway between the catheter 50 and the interior of the delivery cap 100.

As shown in FIGS. 2A–2C, 4A and 4B, a locking clamp 300 is slidably disposed in a slot 130 formed in a base 120 of the delivery cap 100. The slot 130 extends completely through the delivery cap 100 in a transverse direction so that the locking clamp 300 slides back and forth in a plane which is substantially perpendicular to the direction of insert of the cartridge 200.

As shown in FIG. 2A, the cartridge 200 includes a barrel 230 a distal end of which is inserted into the delivery cap 100. The barrel 230 includes a narrow neck portion 240 and a widened portion 250. A raised ridge portion 260 is formed adjacent to the narrow neck portion 240. The narrow neck portion 240, the widened portion 250, and the raised ridge portion 260 are integrally formed with the barrel 230 when the barrel is formed by injection molding.

Figure 3A:
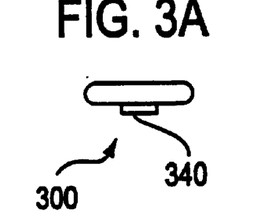
FIGS. 3A, 3B and 3C show the locking clamp.
Figure 3B:
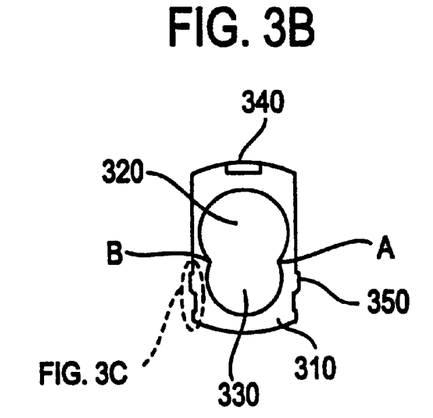

As shown in FIG. 3B, the locking clamp 300 is substantially rectangular shaped and includes two circular holes 320 and 330 formed in a plate 310 such that a portion of the areas of the circular holes overlap, thereby forming a "figure eight" shape. The diameter of the circular hole 320 is larger than the diameter of the widened portion 250 of the barrel 230 (see FIG. 2) so that cartridge 200 can be inserted easily through the hole 320. The diameter of the circular hole 330 is slightly larger than the diameter of the narrow neck portion 240 of the barrel 230, but smaller than the diameter of the widened portion 250 and raised ridge portion 260, so that the widened portion and raised ridge portion cannot slide through the circular hole 330.

Figure 4A:
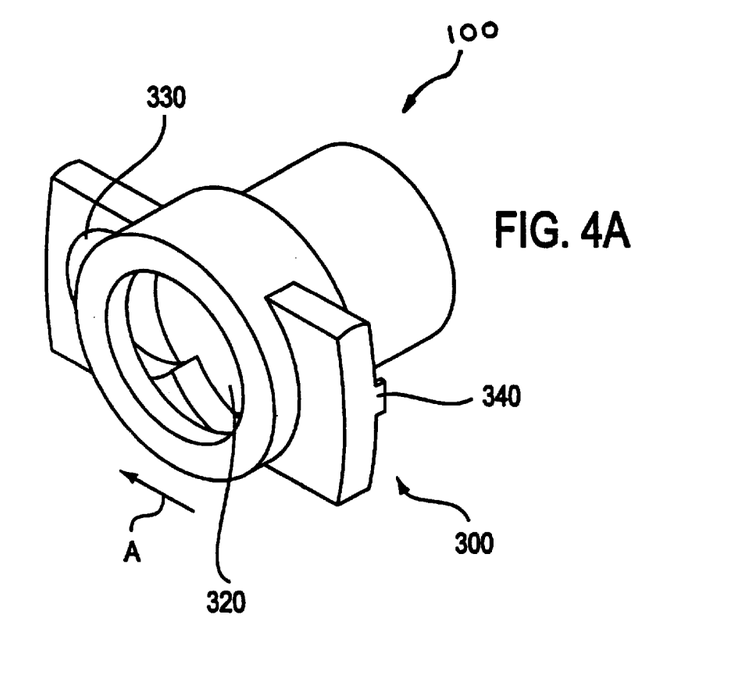
FIGS. 4A and 4B show the operation of the locking clamp.
Figure 4B:
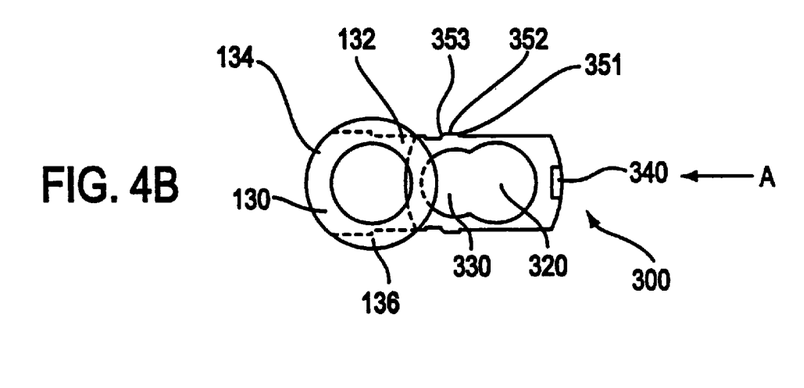

As shown in FIGS. 4A and 4B, the locking clamp 300 is movable between a first position in which the center of the large hole 320 is substantially concentric with the center of the delivery cap 100, and a second position in which the center of the small hole 330 is substantially concentric with the center of the delivery cap 100. Accordingly, when the locking clamp 300 is in the first position, the cartridge 200 can be inserted into the opening 110 of the delivery cap 100.

The locking clamp 300 is located at a position within the delivery cap 100 such that when the cartridge 200 is fully inserted into the delivery cap 100, the locking clamp 300 lines up with the narrow neck portion 240. When the locking clamp 300 is moved to the second position with the cartridge 200 fully inserted in the delivery cap 100, the small hole 330 moves over the narrow neck portion 240 so that the narrow neck portion becomes disposed within the small hole 330. Since the diameters of the widened portion 250 and raised ridge portion 260 are greater than the diameter of the small hole 330, the cartridge 200 becomes locked in the delivery cap 100 and cannot be removed.

The distance between the points at which the circumferences of the large hole 320 and small hole 330 meet (i.e., the length of an imaginary line that connects the discontinuous points of the figure-eight shape, points A and B, and extends across the figure-eight shape) is slightly smaller than the diameter of the narrow neck portion 240. Therefore, when the locking clamp 300 is moved from the first position to the second position, these points contact the narrow neck portion 240. As the locking clamp 300 is further pushed toward the second position, a force is exerted on the small hole 330 at points A and B, thereby expanding the small hole 330. As the locking clamp 300 is further pushed towards the second position, such that the contact points clear the narrow neck portion 240, the locking clamp 300 makes a distinct snapping sound. Further, the user can feel when the locking clamp 300 snaps into the second or locked position. Accordingly, the locking clamp 300 provides the user with a positive indication that the cartridge 200 has been inserted properly into the delivery cap 100 and securely locked.

Figure 3C:
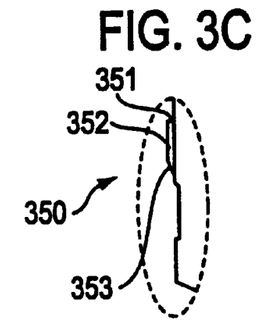

As shown in FIG. 3A, the locking clamp 300 includes a projection 340 disposed on one side of the clamp. When the locking clamp 300 is disposed in the slot 130 in the delivery cap 100, the projection 340 extends higher than the slot 130 so that the projection 340 prevents the locking clamp 300 from sliding out of the slot 130 in direction of arrow A (see FIGS. 4A and 4B). The locking clamp 300 also includes two outer projections 350 which prevent the locking clamp from sliding out of the delivery cap 100 in a direction opposite to the direction of arrow A. As shown in FIG. 3C, the outer projections 350 include an orthogonal surface 351 which is perpendicular to the side surface of the locking clamp 300, a flat surface 352 which extends parallel to a side surface of the locking clamp and a ramped surface 353 which extends from the flat surface 351 to the side of the locking clamp 300.

As shown in FIG. 4B, the slot 130 has a narrow portion 132 having a width that is less than the distance between the outermost edges of the flat surfaces 352, and a widened portion 134 having a width that is greater than the distance between the outermost edges of the flat surfaces 352. A stepped portion 136 is formed at the junction between the narrow portion 132 and the widened portion 134.

When the locking clamp 300 is inserted into the delivery cap 100, the ramped surfaces 353 engage the narrow portion 132. As the locking clamp 300 is further inserted into the slot 130, a force is exerted on the ramping surfaces 353 which causes the locking clamp 300 to deflect inward and slide through the narrow portion 132. When the outer projections 350 reach the widened portion 134, the locking clamp 300 snaps back to its original width and is freely slidable in the slot 130. If the locking clamp 300 is moved in a direction opposite to direction A, the orthogonal surfaces 351 engage the stepped surfaces 136, thereby preventing the locking clamp 300 from sliding out of the slot in the delivery cap 100. The locking clamp 300 can be removed from the delivery cap 100 by forcibly sliding the locking clamp 300 in a direction opposite to arrow A.

A second embodiment of the present invention is shown in FIGS. 10–13. The second 20 embodiment is an injection needle assembly which is used to deliver a highly viscous material directly to a needle. The main difference between the second embodiment and the first embodiment is that the delivery cap is connected directly to a needle rather than a catheter.

Accordingly, many of the components in the second embodiment are identical to those of the first embodiment. Identical components will be denoted by identical reference numerals.

Figure 10:
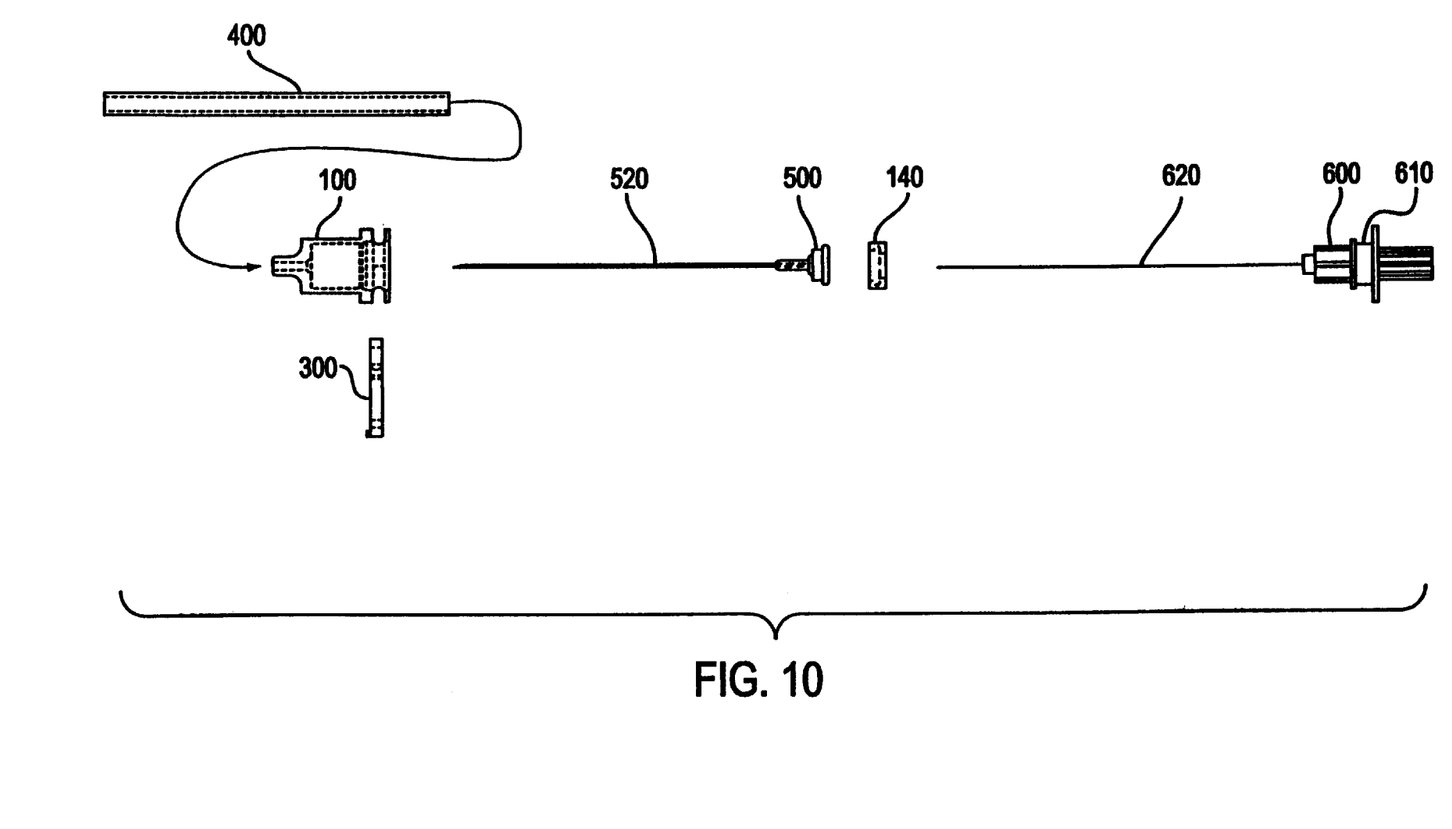
FIG. 10 shows the main components of a second embodiment of the present invention.
Figure 11:
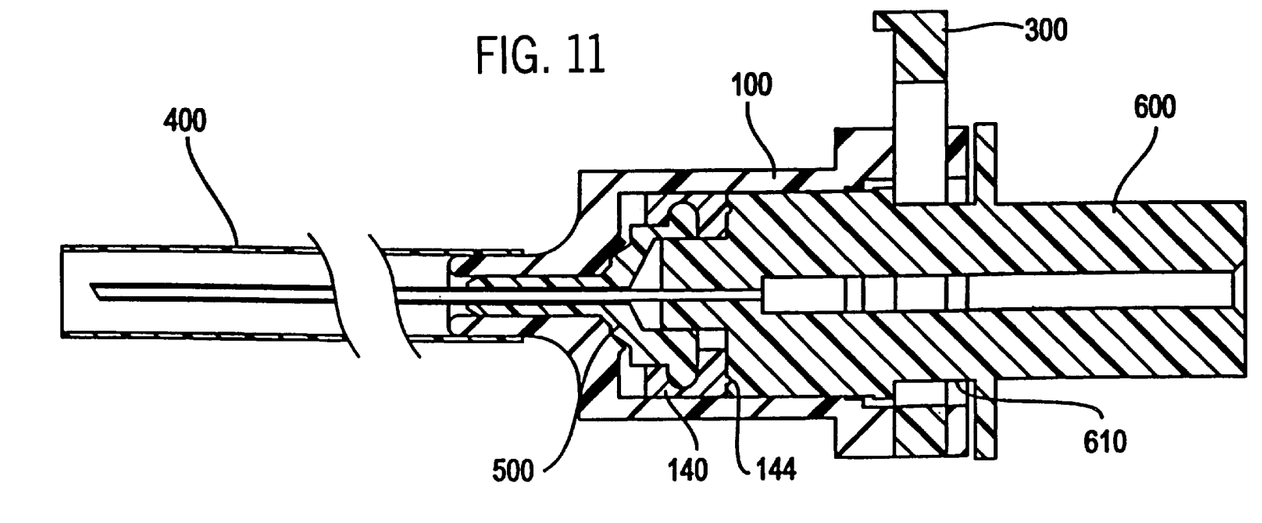
FIG. 11 is a cross-sectional view of the injection needle assembly.
Figure 12:
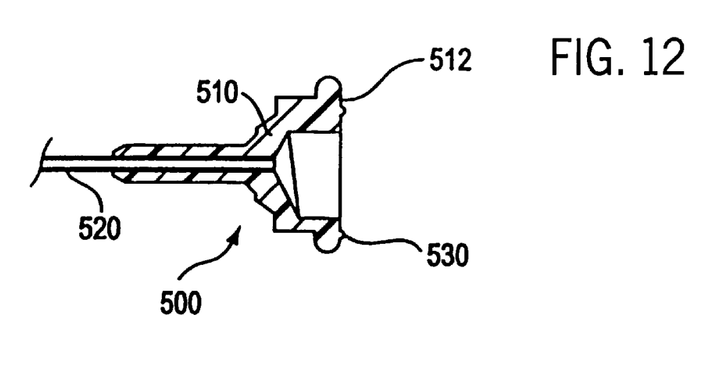
FIG. 12 is a cross-sectional view of the cannula insert of the injection needle assembly.

As shown in FIGS. 10–12, the delivery system of the second embodiment comprises sheath 400, a delivery cap 100 having a locking clamp 300, a cannula insert 500, a compression sleeve 140, and a stylet insert 600. As shown in FIG. 12, the cannula insert 500 comprises a polysulfone hub 510 molded onto a needle 520. A flange portion 512 of the hub 510 is inserted in the wide diameter cut-out portion 142 of the compression sleeve 140, thereby attaching the cannula insert 500 to the compression sleeve 140, as shown in FIG. 11. The cannula insert 500 is contained within, and bonded to, the delivery cap 100 using a solvent bond. The hub 510 has a raised sealing rib 530 for forming a tight seal with the compression sleeve 140. A locking clamp 300 is inserted into the delivery cap 100 to form a needle assembly.

Figure 13:
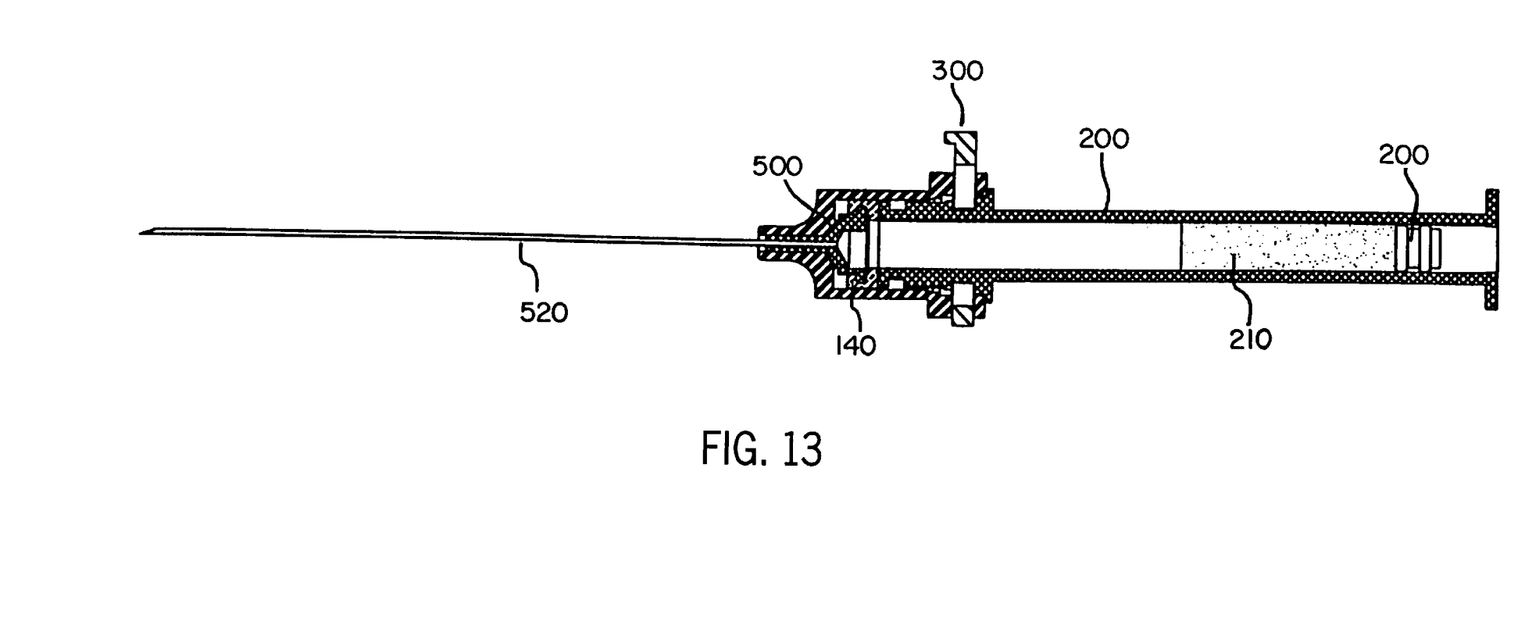
FIG. 13 is a cross-sectional view the injection needle assembly attached to a cartridge.

As shown in FIGS. 10 and 11, the stylet 600 is inserted into the cannula insert 500 for minimizing tissue coring during insertion of the needle. The stylet 600 is secured to the delivery cap 100 by locking the locking clamp 300 to a narrow portion 610 of the stylet. The raised 10 sealing rib 144 of the compression sleeve 140 holds the stylet 600 in the proper position. After insertion, the stylet 600 is removed and the injection needle assembly is connected to a cartridge 200 in order to deliver a material to the needle 520, as shown in FIG. 13.

The above described delivery cap 100, cartridge 200, locking clamp 300 and interconnect insert 150 can be made by injection molding using thermoplastics such as polysulfone, polyetherimide, polypropylene, polycarbonate, etc. which have high hardness and strength and which can withstand sterilization. The compression sleeve 140 can be manufactured from silicone rubber.

Although the present invention is directed to a delivery system for a viscous material, it can also be used to deliver non-viscous materials. For example, the present invention could be used to join IV tubes, instead of using a needle.

As described above, the present invention makes it easy to change syringes and needles due to the easy-to-use sliding lock which does not require a twisting motion. The sliding lock positively notifies the user that the cartridge has been attached properly due to the audible click of the sliding clamp, which ensures that the cartridge will be attached properly. Also, the raised sealing ribs of the compression sleeve and cartridge create a leak-resistant seal between the cartridge and the delivery cap, thereby eliminating leakage of the viscous material. Further, the delivery cap creates a leak-resistant seal between the delivery cap and the catheter.

What is claimed is:

1. A delivery device comprising:
   a delivery cap for delivering a material to a site; and
   a locking clamp slidably disposed in said delivery cap for securing said delivery cap to a cartridge, said locking clamp having a first circular hole and a second circular hole formed therein, said first circular hole being formed by a first circular wall and having a first diameter and said second circular hole being formed by a second circular wall and having a second diameter, wherein said first diameter no longer than said second diameter, said first and second circular walls intersect to form a figure-eight shape.

2. The delivery device as set forth in claim 1, wherein said first diameter is larger than a diameter of an end portion of said cartridge.

3. The delivery device as set forth in claim 2, wherein said second diameter is slightly larger than a diameter of a narrow neck portion of said cartridge and smaller than said diameter of said end portion of said cartridge, thereby locking said cartridge to said delivery cap.

4. The delivery device as set forth in claim 3, wherein said locking clamp is movable between a first position at which a center of said first circle is substantially concentric with a center of said delivery cap and a second position at which a center of said second circle is substantially concentric with a center of said delivery cap.

5. The delivery device as set forth in claim 4, wherein a distance between points at which circumferences of said first and second circular holes intersect is slightly smaller than said diameter of said narrow portion of said cartridge, thereby causing said locking clamp to snap over said narrow portion when said locking clamp is moved to said second position.

6. The delivery device as set forth in claim 1, wherein said locking clamp is disposed in a slot formed in said delivery cap, said slot having a narrow portion and a widened portion, and wherein said locking clamp has outer projections located on opposite sides of said locking clamp, outermost edges of said outer projections being separated by a distance that is greater than a width of said narrow portion and less than a width of said widened portion.

7. The delivery device as set forth in claim 6, wherein said slot further includes stepped portions formed at a junction between said narrow portion and said widened portion, and wherein said outer projections include an orthogonal surface which abuts against said stepped portions, thereby preventing said locking clamp from being removed from said slot.

8. The delivery device as set forth in claim 6, wherein said outer projections include a ramped surface for guiding said lock clamp into said slot.

9. A storage and delivery device comprising:
   a cartridge for storing a material;
   a delivery cap attached to said cartridge for delivering said material to a site; and
   a locking clamp slidably disposed in said delivery cap for securing said delivery cap to said cartridge, said locking clamp having a first circular hole and a second circular hole formed therein, said first circular hole being formed by a first circular wall and having a first diameter and said second circular hole being formed by a second circular wall and having a second diameter, wherein said first and second circular walls intersect to form a figure-eight shape.

10. The delivery device as set forth in claim 9, wherein said first diameter is larger than a diameter of an end portion of said cartridge.

11. The delivery device as set forth in claim 10, wherein said second diameter is slightly larger than a diameter of a narrow neck portion of said cartridge and smaller than said diameter of said end portion of said cartridge, thereby locking said cartridge to said delivery cap.

12. The delivery device as set forth in claim 11, wherein said locking clamp is movable between a first position at which a center of said first circle is substantially concentric with a center of said delivery cap and a second position at which a center of said second circle is substantially concentric with a center of said delivery cap.

13. The delivery device as set forth in claim 12, wherein a distance between points at which circumferences of said first and second circular holes intersect is slightly smaller than said diameter of said narrow portion of said cartridge, thereby causing said locking clamp to snap over said narrow portion when said locking clamp is moved to said second position.

14. The delivery device as set forth in claim 9, wherein said locking clamp is disposed in a slot formed in said delivery cap, said slot having a narrow portion and a widened portion, and wherein said locking clamp has outer projections located on opposite sides of said locking clamp, outermost edges of said outer projections being separated by a distance that is greater than a width of said narrow portion and less than a width of said widened portion.

15. The delivery device as set forth in claim 14, wherein said slot further includes stepped portions formed at a junction between said narrow portion and said widened portion, and wherein said outer projections include an orthogonal surface which abuts against said stepped portions, thereby preventing said locking clamp from being removed from said slot.

16. The delivery device as set forth in claim 14, wherein said outer projections include a ramped surface for guiding said lock clamp into said slot.

17. A delivery cap for a storage and delivery device comprising:
   a locking clamp slidably disposed in said delivery cap for securing a cartridge thereto;
   an interconnect insert positioned adjacent to a nose portion of said delivery cap;
   a catheter disposed in said nose portion and connected to said interconnect insert for delivering a material to an remote site; and
   a compression sleeve connected to said interconnect insert for forming a sealing surface with said cartridge.

18. A delivery cap for a storage and delivery device comprising:
   an interconnect insert positioned adjacent to a nose portion of said delivery cap;
   a catheter disposed in said nose portion and connected to said interconnect insert for delivering a material to an remote site; and
   a compression sleeve connected to said interconnect insert for forming a sealing surface with a cartridge.

19. The delivery cap of claim 18, wherein said catheter has flaring portions wedged between said interconnect insert and said nose portion of said delivery cap.

20. The delivery cap of claim 19, wherein said flaring portions are disposed in a cut-out section formed in a base of said nose portion of said delivery cap.

21. The delivery cap of claim 18, wherein said interconnect insert includes a raised sealing rib for forming a tight seal between said interconnect insert and said compression sleeve.

22. The delivery cap of claim 21, wherein said compression sleeve includes a raised sealing rib formed on a lower face for forming a tight seal with said cartridge.

23. The delivery cap of claim 22 wherein said raised sealing rib of said compression sleeve is circular with a diameter that is larger than a diameter of a raised sealing rib of said cartridge.

24. The delivery cap of claim 18, wherein said interconnect insert includes a flange portion and said the compression sleeve includes a wide diameter cut-out portion, and wherein said cut-out portion receives said flange portion, thereby attaching the interconnect insert to the compression sleeve.

25. The delivery cap of claim 17, wherein said locking clamp has a first circular hole with a first diameter and a second circular hole with a second diameter formed therein, and wherein said first and second circular hole intersect to form a figure-eight shape.

26. A delivery device comprising:
a delivery cap having a nose portion;
a locking clamp slidably disposed in said delivery cap for securing said delivery cap to a cartridge;
an interconnect insert positioned adjacent to said nose portion of said delivery cap;
a catheter disposed in said nose portion and connected to said interconnect insert for delivering a material to an remote site; and
a compression sleeve connected to said interconnect insert for forming a sealing surface with said cartridge.

27. The delivery cap of claim 26, wherein said catheter has flaring portions wedged between said interconnect insert and said nose portion of said delivery cap.

28. The delivery cap of claim 27, wherein said flaring portions are disposed in a cut-out section formed in a base of said nose portion of said delivery cap.

29. The delivery cap of claim 26, wherein said interconnect insert includes a raised sealing rib for forming a tight seal between said interconnect insert and said compression sleeve.

30. The delivery cap of claim 29, wherein said compression sleeve includes a raised sealing rib formed on a lower face for forming a tight seal with said cartridge.

31. The delivery cap of claim 30 wherein said raised sealing rib of said compression sleeve is circular with a diameter that is larger than a diameter of a raised sealing rib of said cartridge.

32. The delivery cap of claim 26, wherein said interconnect insert includes a flange portion and said the compression sleeve includes a wide diameter cut-out portion, and wherein said cut-out portion receives said flange portion, thereby attaching the interconnect insert to the compression sleeve.

33. The delivery cap of claim 26 wherein said locking clamp has a first circular hole with a first diameter and a second circular hole with a second diameter formed therein, and wherein said first and second circular hole intersect to form a figure-eight shape.

34. A delivery cap for a storage and delivery device comprising:
a tubular member disposed in a nose portion of a delivery cap for delivering a material to an remote site;
an interconnect insert positioned adjacent to said nose portion; and
a compression sleeve connected to said interconnect insert for forming a sealing surface with a cartridge.

35. The delivery cap of claim 34, wherein said tubular member is a catheter.

36. The delivery cap of claim 34, wherein said tubular member is a needle.

37. An injection needle assembly for a storage and delivery device comprising:
a delivery cap;
a locking clamp slidably disposed in said delivery cap;
a cannula insert positioned within a nose portion of said delivery cap, said cannula insert having a needle disposed in a central portion thereof for delivering a material to an remote site; and
a compression sleeve connected to said cannula insert for forming a sealing surface with a cartridge.

38. A delivery device comprising:
a delivery cap for delivering a material to a site; and
a locking clamp slidably disposed in said delivery cap for securing said delivery cap to a cartridge, said locking clamp having a first circular hole and a second circular hole formed therein, said first circular hole being formed by a first circular wall and having a first diameter and said second circular hole being formed by a second circular wall and having a second diameter, wherein said first diameter is larger than said second diameter, said first and second circular walls intersect to form a figure-eight shape, and a distance between points at which said first and second circular holes intersect is slightly smaller than a diameter of a narrow neck portion of said cartridge, thereby enabling said locking clamp to snap over said narrow portion.

39. A delivery cap for a storage and delivery device comprising:
a locking clamp slidably disposed in said delivery cap for securing said delivery cap to a cartridge, said locking clamp having a first hole formed by a first arcuate wall and a second hole formed by a second arcuate wall formed therein, wherein said first and second arcuate walls intersect at opposing locations in said locking clamp to form a figure-eight shape and wherein a distance between points at which said first and second arcuate walls intersect is slightly smaller than a diameter of a narrow neck portion of said cartridge, thereby enabling said locking clamp to snap over said narrow portion.

40. A storage and delivery device comprising:
a cartridge for storing a material;
a delivery cap attached to said cartridge for delivering said material to a site; and
a locking clamp slidably disposed in said delivery cap for securing said delivery cap to said cartridge, said locking clamp having a first circular hole and a second circular hole formed therein, said first circular hole being formed by a first circular wall and having a first diameter and said second circular hole being formed by a second circular wall and having a second diameter, wherein said first and second circular walls intersect to form a figure-eight shape and wherein a distance between points at which said first and second circular holes intersect is slightly smaller than a diameter of a narrow neck portion of said cartridge, thereby enabling said locking clamp to snap over said narrow portion.

* * * * *

UNITED STATES PATENT AND TRADEMARK OFFICE
CERTIFICATE OF CORRECTION

PATENT NO. : 6,132,402
DATED : October 17, 2000
INVENTOR(S) : Tessmann et al.

It is certified that error appears in the above-identified patent and that said Letters Patent is hereby corrected as shown below:

Column 7,
Line 21, "no longer" should be -- is larger --.

Column 8, claim 17,
Line 55, "an" should be -- a --.

Column 8, claim 18,
Line 64, "an" should be -- a --.

Column 9, claim 24,
Line 17, "the" should be deleted.

Column 9, claim 32,
Line 55, "the" should be deleted.

Column 9, claim 34,
Line 67, "an" should be -- a --.

Column 10, clam 37,
Line 17, "an" should be --a --.

Signed and Sealed this

Twelfth Day of February, 2002

Attest:

JAMES E. ROGAN
*Attesting Officer*   *Director of the United States Patent and Trademark Office*